(12) United States Patent
Palmer et al.

(10) Patent No.: US 8,029,661 B2
(45) Date of Patent: Oct. 4, 2011

(54) METHOD FOR ON-LINE MONITORING OF WAX CRYSTALLIZATION

(75) Inventors: Thomas R. Palmer, Houston, TX (US);
Brent E. Beasley, Fairfax, VA (US);
David S. Sinclair, Houston, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 309 days.

(21) Appl. No.: 12/312,054

(22) PCT Filed: Oct. 19, 2007

(86) PCT No.: PCT/US2007/022373
§ 371 (c)(1),
(2), (4) Date: Apr. 22, 2009

(87) PCT Pub. No.: WO2008/051492
PCT Pub. Date: May 2, 2008

(65) Prior Publication Data
US 2010/0065469 A1    Mar. 18, 2010

(51) Int. Cl.
*C10G 73/08* (2006.01)

(52) U.S. Cl. ............... 208/28; 208/27; 208/30; 208/31; 208/33; 208/35; 196/14.5; 377/11; 250/222.1; 356/335; 356/336; 356/337; 356/338; 356/339; 356/340; 356/341; 356/342; 356/343

(58) Field of Classification Search ................ 208/27, 208/30–31, 33, 35; 250/222.1; 377/11; 356/335–343; 196/14.5
See application file for complete search history.

(56) References Cited

U.S. PATENT DOCUMENTS

| | | | | |
|---|---|---|---|---|
| 3,764,517 A | * | 10/1973 | Bodemuller, Jr. ............ | 208/33 |
| 3,773,650 A | * | 11/1973 | Hislop et al. ................ | 208/33 |
| 3,972,779 A | * | 8/1976 | Harrison ..................... | 196/14.5 |
| 4,885,062 A | * | 12/1989 | Harrison et al. ............ | 196/14.5 |
| 2006/0173230 A1 | * | 8/2006 | Chang et al. ................ | 585/638 |

* cited by examiner

*Primary Examiner* — Walter Griffin
*Assistant Examiner* — Brian McCaig
(74) *Attorney, Agent, or Firm* — Robert A. Migliorini (57) ABSTRACT

The determination of wax crystal particle size and population is used to monitor the performance of wax crystallizers used in lubricant oil processing using solvent dewaxing. The wax crystal particle size is monitored using online measurements. The information obtained from on-line monitoring is then used to control crystallization in the dewaxing equipment in order to optimize performance of the dewaxing units.

21 Claims, 5 Drawing Sheets

Figure 5

METHOD FOR ON-LINE MONITORING OF WAX CRYSTALLIZATION

FIELD OF THE INVENTION

This invention relates to the use of wax crystal particle size and population to monitor the performance of wax crystallizers used in solvent dewaxing for lubricant oil processing. The wax crystal particle size is monitored using on-line measurements. The information obtained from on-line monitoring is then used to control crystallization in the dewaxing equipment in order to optimize performance of the dewaxing units.

BACKGROUND OF THE INVENTION

Higher molecular weight hydrocarbon fractions used as feedstocks to prepare lubricating oil basestocks typically have an initial boiling point in 343° C.+ range. These feedstocks usually contain wax, irrespective of whether the fraction is derived from natural or synthetic sources. Most wax containing feedstocks are derived from naturally occurring sources, such as petroleum, bitumen and the like, but in the future more and more will be derived from synthetic crudes and hydrocarbon fractions produced by processes such as gas conversion, wherein natural gas or a gas comprising primarily methane is converted to a synthesis gas which, in turn, is used to synthesize hydrocarbons. The trend to lubricating oils having higher VI to meet government mandated standards leads to feedstocks having increasing wax contents. Basestocks meeting the Group I classification for motor oils are typically prepared using solvent techniques, while Groups II and III basestocks typically utilize catalytic techniques.

Feedstocks boiling in the range of from about 343 to about 566° C. or greater are used to prepare lubricating oils for motor vehicles, turbines, machining and the like. In order for a lubricating oil fraction to be useful as a lubricating oil base stock, the wax must be at least partially removed. This is accomplished by either solvent dewaxing or catalytic dewaxing. Most dewaxing facilities used to prepare Group I basestocks still employ solvent dewaxing, in which a chilled dewaxing solvent is slowly mixed with the lubricating oil fraction and the mixture slowly cooled, under conditions of agitation, down to the desired cloud or pour point temperature. Group II basestocks are typically prepared using either solvent or catalytic techniques. Group III and higher basestocks are prepared using catalytic techniques for dewaxing.

One method of dilution chilling dewaxing is the DILCHILL$^{SM}$ process (DILCHILL$^{SM}$ is a registered Service Mark of ExxonMobil Research and Engineering Company). DILCHILL$^{SM}$ is disclosed in U.S. Pat. No. 3,773,650. A number of improvements and modifications have been made to the basic concept of DILCHILL. For example it has been shown that in a vertically staged cooling tower, the velocity of the solvent at the injection points within each stage should be at least 5-30 times that of the peripheral velocity of the mixer blades. This results in greater filtration rates and higher dewaxed oil yields than could otherwise be obtained without the relatively high velocity solvent injection. It has also been shown that a combination of dilution chilling with scraped surface chilling is useful for dewaxing lubricating oils. Other methods teach adjusting the dewaxing solvent composition so that the waxy oil and solvent are immiscible near the last stage of the cooling zone. This results in superior dewaxed oil yields and higher filter rates when the waxy oil stock being fed to the tower is relatively high in viscosity and molecular weight. It is also known to partially predilute the waxy oil when the oil is a relatively heavy feed such as a resid or a bright stock before the oil is introduced into the chilling zone. However, in all of these DILCHILL$^{SM}$ dewaxing processes, it was thought that the rate of solvent addition to each stage should be adjusted so as to obtain the same or approximately equal temperature drops in each stage.

It is known that the DILCHILL$^{SM}$ process is improved when the waxy lube oil stocks are solvent dewaxed by contacting them with successive increments of cold dewaxing solvent at a plurality of points along the height of a vertical tower divided into a plurality of stages while agitating the oil solvent mixture in each stage to provide substantially instantaneous mixing of the waxy oil and solvent thereby precipitating wax from the oil. The well known shock chilling effect is avoided by adjusting the cold solvent addition to each stage in a manner so as to modify the temperature profile along the tower to ensure that the temperature drop per stage in the initial stages in which wax precipitation occurs is greater than the temperature drop per stage in the final or later stages in which wax precipitation occurs.

Various methods have been proposed to monitor wax crystallization. In one method, a laser beam reflected by wax crystals is used in determining the wax crystallization temperature of a hot dewaxing solvent upstream of solvent chillers. This is automatically achieved by an on-line method from a remote control point, in which a slipstream of solvent is passed through an attached solvent loop into a sample chamber in the loop, without being exposed to ambient conditions. As the sample is cooled, the beam reflections are detected and indicate the wax to crystallization temperature. Corrective measures can then be taken to prevent fouling of the chillers, if need be. Another method uses an electronic analyzer which involves the transmission of light or in the degree or intensity of reflected light associated with wax formation.

The above methods are directed to analyzing for total wax content. There is still a need to monitor the effectiveness of the wax crystallization process itself, especially as it relates to crystal size distributions.

SUMMARY OF THE INVENTION

In one embodiment, this invention relates to a process for on-line monitoring of wax crystal formation in solvent dewaxing equipment for use in lubricant oil production, said solvent dewaxing equipment including at least one chilling tower, which comprises: conducting a waxy feedstock to the at least one chilling tower having at least one inlet and outlet, contacting the waxy feedstock with chilled dewaxing solvent to form a mixture of solvent, oil and wax crystals, conducting the mixture from the at least one chilling tower outlet to a separator provided that wax crystal size distribution of the wax crystals in the mixture is measured prior to entering the separator using an on-line particle size analyzer, and separating wax crystals from oil and solvent.

Another embodiment relates to a solvent dewaxing process for the preparation of lubricant oils from a waxy feedstock which comprises: conducting the waxy feedstock to at least one chilling tower having at least one inlet and outlet, contacting the waxy feedstock with dewaxing solvent in at least one chilling zone in the chilling tower under mixing conditions to form a mixture of wax crystals, solvent and oil, conducting the mixture from the at least one chilling tower outlet to a separator provided that wax crystal size distribution of the wax crystals in the mixture is measured prior to entering the separator using an on-line particle size analyzer, separating wax crystals from oil and solvent, and adjusting conditions as needed in the at least one chilling tower to modify wax crystal size to improve separation of wax crystals.

DETAILED DESCRIPTION OF THE INVENTION

Feedstock Preparation

The solvent refining of select crude oils to produce lubricating oil basestocks typically involves atmospheric distillation, vacuum distillation, extraction, dewaxing and hydrofinishing. Because basestocks having a high isoparaffin content are characterized by having good viscosity index (VI) properties and suitable low temperature properties, the crude oils used in the solvent refining process are typically paraffinic crudes. One method of classifying lubricating oil basestocks is that used by the American Petroleum Institute (API). API Group I basestocks are produced by solvent refining of lubricant basestocks and still represent a sizeable part of the worldwide lubricant market. API Group II basestocks have a saturates content of 90 wt. % or greater, a sulfur content of not more than 0.03 wt. % and a viscosity index (VI) greater than 80 but less than 120. Group II basestocks typically involve hydroprocessing and may also include solvent refining as part of the manufacturing process.

In solvent refining, the high boiling petroleum fractions from atmospheric distillation are sent to a vacuum distillation unit, and the distillation fractions from this unit are solvent extracted. The residue from vacuum distillation which may be deasphalted is sent to other processing. Other feeds that may be solvent extracted include waxy streams such as dewaxed oils and foots oils.

The solvent extraction process selectively dissolves the aromatic components in an extract phase while leaving the more paraffinic components in a raffinate phase. Naphthenes are distributed between the extract and raffinate phases. Typical solvents for solvent extraction include phenol, furfural and N-methyl pyrrolidone. By controlling the solvent to oil ratio, extraction temperature and method of contacting distillate to be extracted with solvent, one can control the degree of separation between the extract and raffinate phases.

The raffinate from the solvent extraction may be under-extracted, i.e., the extraction is carried out under conditions such that the raffinate yield is maximized while still removing most of the lowest quality molecules from the feed. Raffinate yield may be maximized by controlling extraction conditions, for example, by lowering the solvent to oil treat ratio and/or decreasing the extraction temperature. The raffinate from the solvent extraction unit is usually solvent dewaxed under solvent dewaxing conditions to remove hard waxes from the raffinate from the solvent extraction unit.

Hydrotreating

Raffinate feedstocks frequently contain sulfur and/or nitrogen contaminants in an amount unacceptable for lube oils. Accordingly, if the raffinate feedstock contains unacceptable amounts of sulfur and/or nitrogen contaminants, such feedstock may be contacted with a hydrotreating catalyst under conditions effective to remove at least a portion of the sulfur and/or nitrogen contaminants to produce a hydrotreated feedstock. Hydrotreating catalysts suitable for use herein are those containing at least one Group 6 (based on the IUPAC Periodic Table having Groups 1-18) metal and at least one Groups 8-10 metal, including mixtures thereof. Preferred metals include Ni, W, Mo, Co and mixtures thereof. These metals or mixtures of metals are typically present as oxides or sulfides on refractory metal oxide supports. The mixture of metals may also be present as bulk metal catalysts wherein the amount of metal is 30 wt % or greater, based on catalyst.

Suitable metal oxide supports include oxides such as silica, alumina, silica-alumina or titania, preferably alumina. Preferred aluminas are porous aluminas such as gamma or eta. The acidity of metal oxide supports can be controlled by adding promoters and/or dopants, or by controlling the nature of the metal oxide support, e.g., by controlling the amount of silica incorporated into a silica-alumina support. Examples of promoters and/or dopants include halogen, especially fluorine, phosphorus, boron, yttria, rare-earth oxides and magnesia. Promoters such as halogens generally increase the acidity of metal oxide supports while mildly basic dopants such as yttria or magnesia tend to decrease the acidity of such supports.

It should be noted that bulk catalysts typically do not include a support material, and the metals are not present as an oxide or sulfide but as the metal itself. These catalysts typically include metals within the range described above in relation to bulk catalyst and at least one extrusion agent. The amount of metals for supported hydrotreating catalysts, either individually or in mixtures, ranges from 0.5 to 35 wt %, based on catalyst. In the case of preferred mixtures of Group 6 and Groups 8-10 metals, the Group 8-10 metals are present in amounts of from 0.5 to 5 wt %, based on catalyst and the Group 6 metals are present in amounts of from 5 to 30 wt %. The amounts of metals may be measured by atomic absorption spectroscopy, inductively coupled plasma-atomic emission spectrometry or other methods specified by ASTM for individual metals. Non-limiting examples of suitable commercially available hydrotreating catalysts include RT-721, KF-840, KF-848, and Sentinel™. Preferred catalysts are low acidity, high metals content catalysts including KF-848 and RT-721.

Hydrotreating conditions involve temperatures in the range 280° C. to 400° C., preferably 300° C. to 380° C. at pressures in the range of 1480 to 20786 kPa (200 to 3000 psig), preferably 2859 to 13891 kPa (400 to 2000 psig), a space velocity of from 0.1 to 10 LHSV, preferably 0.1 to 5 LHSV, and a hydrogen treat gas rate of from 89 to 1780 m$^3$/m$^3$ (500 to 10000 scf/B), preferably 178 to 890 m$^3$/m$^3$ (1000 to 5000 scf/B).

Hydrotreating typically reduces nitrogen and sulfur contaminants in the feedstock by converting these contaminants to ammonia and hydrogen sulfide, respectively. These gaseous contaminants may be separated from the hydrotreated feedstock using conventional techniques such as strippers, knock-out drums and the like. In the alternative, if the hydrotreated effluent from the hydrotreater contains amounts of contaminants that will not interfere with the subsequent dewaxing stages, the entire gaseous and liquid effluent from the hydrotreater may be sent to the dewaxing stage.

The hydrotreating reaction stage can be comprised of one or more fixed bed reactors or reaction zones each of which can comprise one or more catalyst beds of the same hydrotreating catalyst. Although other types of catalyst beds can be used, fixed beds are preferred. Such other types of catalyst beds include fluidized beds, ebullating beds, slurry beds, and moving beds. Interstage cooling or heating between reactors or reaction zones, or between catalyst beds in the same reactor or reaction zone, can be employed since the desulfurization reaction is generally exothermic. A portion of the heat generated during hydrotreating can be recovered. Where this heat recovery option is not available, conventional cooling may be performed through cooling utilities such as cooling water or air, or through use of a hydrogen quench stream. In this manner, optimum reaction temperatures can be more easily maintained.

During hydrotreating, less than 5 wt % of the feedstock, preferably less than 3 wt %, more preferably less than 2 wt %, is converted to 650° F. (343° C.) minus products to produce a hydrotreated feedstock whose VI increase is less than 4, preferably less than 3, more preferably less than 2 greater than the VI of the feedstock.

Solvent Dewaxing

Solvent dewaxing typically involves mixing the raffinate feed (which may be hydrotreated) from the solvent extraction unit with chilled dewaxing solvent to form an oil-solvent solution. Upon further chilling, precipitated wax is separated by, for example, filtration. The temperature and solvent are selected so that the oil is dissolved by the chilled solvent while the wax is precipitated.

A particularly suitable solvent dewaxing process involves the use of a cooling tower where solvent is prechilled and added incrementally at several points along the height of the cooling tower. The oil-solvent mixture is agitated during the chilling step to permit substantially instantaneous mixing of the prechilled solvent with the oil. The prechilled solvent is added incrementally along the length of the cooling tower so as to maintain an average chilling rate at or below 10° F./minute (5.6° C./minute), usually between about 1 to about 5° F./minute (0.6 to 2.8° C./minute). The final temperature of the oil-solvent/precipitated wax mixture in the cooling tower will usually be between 0 and 50° F. (−17.8 to 10° C.). The mixture may then be sent to a scraped surface chiller for further chilling and then to a filtration system to separate precipitated wax from the mixture. Further details on incremental solvent dilution chilling may be found in U.S. Pat. No. 5,401,383 which is incorporated herein in its entirety.

In general, the amount of solvent added will be sufficient to provide a liquid/solid weight ratio between the range of 5/1 and 20/1 at the dewaxing temperature and a solvent/oil volume ratio between 1.5/1 to 5/1. The solvent dewaxed oil is typically dewaxed to an intermediate pour point, preferably less than about +10° C. Representative dewaxing solvents are aliphatic ketones having 3-6 carbon atoms such as methyl ethyl ketone and methyl isobutyl ketone, low molecular weight $C_3$-$C_6$ hydrocarbons such as propane and butane, and mixtures thereof. The solvents may be mixed with other aromatic solvents such as benzene, toluene or xylene.

As the mixture is cooled, wax crystals precipitate out, to form a slurry of wax crystals in the cold mixture of solvent and oil. Adding dewaxing solvent to the waxy oil also lowers the viscosity of the mixture. In many cases, a mixture of a wax solvent, such as toluene, and a wax antisolvent, typically comprising ketones such as methyl ethyl ketone and methyl isobutyl ketone, are used to reduce the solubility of the wax in the oil while avoiding oil immiscibility at the wax separation temperature. The wax is preferably separated from the mixture of oil and solvent by filtration, e.g., by using rotary vacuum filters or membrane filters. Centrifugation and filter clothes are other method for separating wax. The oily filtrate and wax precipitate are passed to separate fractionators, to separate and recover the dewaxing solvent from the dewaxed oil and the wax. The hot dewaxing solvent recovered from the fractionators is passed to indirect heat exchangers referred to as chillers, to lower its temperature sufficient for dewaxing. This temperature is lower than the dewaxing temperature.

Wax entrained or carried over with the solvent in the solvent recovery fractionators often causes fouling in the downstream dewaxing solvent chillers. The fouling comprises wax precipitation and the formation of a layer of wax on the interior heat exchange surfaces of the chillers, which acts as thermal insulation. As a consequence, the temperature of the dewaxing solvent exiting the chillers becomes too high for the downstream dewaxing operation. The chillers must then be taken off-line and cleaned, and this reduces plant capacity. A common way of checking for wax in the chilled solvent is for an operator to take a sample of hot solvent upstream of the chillers, slowly cool it, and visually determine the temperature at which wax crystals form. This method is not optimal and there is no control over the conditions. Taking a sample of hot solvent can be a fire hazard and, further, solvent evaporation while talking the sample can produce an artificially high wax crystallization temperature. In order to make the determination, the sample must be brought to a laboratory or other facility to make the determination. The hot sample is then slowly cooled and the temperature monitored, while watching for wax crystal formation. The temperature at which wax crystals begin to form is taken as the wax crystallization temperature. This method takes too much time to be useful for on-line or real time monitoring.

On-Line Monitoring

In one embodiment, the present process relates to a controlled and relatively quick, on-line detection technique capable of detecting the population, formation and size of wax crystals. This would enable an operator to optimize the performance of the dewaxing unit and eliminate or reduce unnecessary chilling or dilution thus minimizing energy and solvent costs. The preferred method of dilution chilling dewaxing is the DILCHILL$^{SM}$ process.

The typical solvent dewaxing process occurs using a multiplicity of chilling towers. The oil-solvent mixture with precipitated wax passing from the final stage of the chilling tower is conducted to a means for separating the wax from the wax containing mixture. Any suitable means for such separation may be employed, such as filtration or centrifugation. In general, filtration is a preferred means of separation, and any filter suitable for separating wax from oil and solvent may be used. The oil-solvent mixture leaving the wax separation means is sent to further processing such as solvent recovery. The separated wax then passes through additional refining and solvent recovery operations.

Suitable filters for separating wax from oil include rotary drum filters and membrane filters. Rotary drum filters are well known and a typical rotary drum filter is preferably a rotary drum vacuum filter containing a drum and a filtering medium such as a filter cloth. The drum includes means for applying pressure and/or vacuum across the filtering medium wherein an oily filtrate is drawn through the filtering medium and a waxy cake is deposited thereon. The waxy cake is washed with solvent and removed from the filter. An example of membrane filtration is the MAX-DEOIL™ process available from ExxonMobil. In this process, a waxy feed containing solvent is chilled and hard wax removed by filters. The soft wax filtrate is then conducted to membrane filters. The permeate from the membrane is mostly solvent while the retentate is mostly soft wax. The permeate is sent to solvent recovery while the retentate is send to wax recovery.

In the present process, a probe is used to monitor wax crystal size in the wax-containing stream in, or the effluent from at least one, preferably all of the chilling towers. Such probes to monitor crystal size distribution are commercially available. An example of such a probe is the Lasentec® FBRM D600 instrument manufactured by Mettler Toledo. Other probes for monitoring crystal size include Malvern's Insitec series analyzers and Beckman Coulter's LS series analyzers. The probe inserted into the wax-containing stream in or from the chilling tower can be inserted at any stage of the chilling tower or at the chilling tower outlet or the inlet to the filters and provides a real-time method for evaluating wax crystal size. Preferred position for the probe is between the chilling tower outlet and the inlet to the filter, especially at or near the chilling tower outlet. In general, larger wax crystals are beneficial to increased productivity as both affect the filterability of the subsequent wax cake formed during filtration.

The crystal size distribution (CSD) is determined by the on-line probe. The skilled operator will have several variables available to control operation within the chilling tower to increase productivity. The precise mix of variables may be influenced by the nature of the feed to the tower. Variables include:

1) Hot wash the tower with warm solvent—this provides a method to melt wax build-up in the trays of the tower that may be causing poor mixing or poor distribution of the cold solvent used to grow the crystals.

2) Increase mixing impeller speed—provides increased mixing of the cold solvent to allow for increased nucleation and growth of wax crystals, this has a side effect when too high an impeller speed causes the shearing of wax crystals breaking them into smaller crystals and reducing the filterability of the wax and the tower production.

3) Adjusting solvent flow, preferably by increasing solvent flow, or adjusting temperature—the main advantage of the DILCHILL$^{SM}$ unit is the abundance of cold solvent to allow the crystals sufficient time and space to nucleate and grow. A low CSD could be caused by insufficient cold solvent.

4) Change the temperature profile down the tower—there can be an optimal temperature ramp as you proceed down the tower that allows for the maximum nucleation of wax crystals at the top of the tower and sufficient cooling to grow the crystals before they exit the tower at the bottom.

The filtration rate and the yield of base oil are correlated with the CSD. Overall profitability is improved if the CSD can be changed to I) maximize throughput, II) maximize yield or III) reduce energy. The cases are feed dependent and the process variable solution set is unique to a particular set of circumstances.

I. If it is desired to maximize throughput, then the skilled operator will consider whether the circumstances are filtration limited or chilling limited.

Ia) Filtration Limited:
When filtration limited, the goal is to increase the filtration rate. Typically Brightstock, 600N and some 250N's may be limited by filtration. When the plant is filtration limited, knowledge of the CSD will allow the operators (or control system) to operate the chiller to control the CSD to produce a high filtration rate. The preferred CSD will have the following key properties a) narrow size distribution (low standard deviation/mean), b) large mean crystal size providing the highest population of the largest crystals possible, c) spherical, and d) "hard" (not soft) crystals that will not deform or break during the filtration process—spherical crystals promote this quality.

Key variables that the operator (or control system) can adjust will include:
1) Predilution ratio,
2) slop to feed ratio,
3) Tower inlet temperature,
4) Agitator speed
5) Tower dilution ratio,
6) Tower temperature profile,
7) Solvent composition
8) Solvent flow profile
9) Solvent temperature(s),
10) Dewaxing aid ratio,
11) Dewaxing aid rate.

The value of these variables depends on the type of feed. There may be a different, unique combination for each type of feed. Feed composition, distillation curve shape, and endpoint are examples of variables that will affect the CSD and require operating parameter adjustments to optimize. The operator (or control system) will evaluate the importance of the individual variable and make adjustments as appropriate to the particular set of circumstances.

Ib) Chilling Limited:
Light grades are not usually considered to be filtration limited. Rather, they are considered to be chilling limited. Typically the goal is to maximize yield (minimize oil-in-wax). The average crystal size will be larger but the distribution may still be broad. Thus the goal will be to change the shape of the CSD, using the variables described above to produce a CSD that will allow the plant to optimize the yield. As noted previously, the preferred CSD will have the following key properties a) narrow size distribution (low standard deviation/mean) b) large mean size providing the highest population of the largest crystals possible c) spherical, and d) "hard" (not soft) crystals that will not deform or break during the filtration process—spherical crystals promote this quality.

II. If it is desired to maximize yield, this objective will be directed to the circumstance of whether the plant is running on set rates (not max rate signal). The same process variables as above for maximum throughput but with a different objective.

III. Energy savings is an objective in principle; however this has not been an objective that is pursued with any frequency. However, the process variables would be the same as set forth above.

In most solvent dewaxing plants, there is normally more than one chilling tower. Thus the CSD determination may be made on the basis of the performance of each individual chilling tower, and the objectives to 1) maximize throughput, 2) maximize yield or 3) reduce energy may be evaluated based on the performance of the tower in question.

On-line monitoring can be integrated into the overall operation of a solvent dewaxing plant as follows. As noted above, feedstock preparation for solvent dewaxing normally involves solvent extracting a waxy feedstock. The raffinate from solvent extracting may then be hydrotreated as discussed above if the raffinate contains excessive nitrogen- and sulfur containing contaminants. Raffinate, including hydrotreated raffinate, is then solvent dewaxed as discussed above. The operation of chilling towers incorporates on-line monitoring to measure wax crystal size according to the present invention. Wax from the effluent from the final chilling tower is separated from oil/solvent. Solvent is stripped from the oil, and the oil may be hydrofinished if needed for product quality issues.

Hydrofinishing

Hydrofinishing is a form of mild hydrotreating directed to saturating any lube range olefins and residual aromatics as well as to removing any remaining heteroatoms and color bodies. Generally the hydrofinishing will be carried out at temperatures from about 150° C. to 350° C., preferably 180° C. to 250° C. Total pressures are typically from 2859 to 20786 kPa (about 400 to 3000 psig). Liquid hourly space velocity is typically from 0.1 to 5 hr.$^{-1}$, preferably 0.5 to 3 hr.$^{-1}$ and hydrogen treat gas rates of from 44.5 to 1780 m$^3$/m$^3$ (250 to 10,000 scf/B).

Hydrofinishing catalysts are those containing Group 6 metals (based on the IUPAC Periodic Table format having Groups from 1 to 18), Groups 8-10 metals, and mixtures thereof. Preferred metals include at least one noble metal having a strong hydrogenation function, especially platinum, palladium and mixtures thereof. The mixture of metals may also be present as bulk metal catalysts wherein the amount of metal is 30 wt % or greater based on catalyst. Suitable metal oxide supports include low acidic oxides such as silica, alumina, silica-aluminas or titania, preferably alumina. The preferred hydrofinishing catalysts for aromatics saturation will comprise at least one metal having relatively strong hydrogenation function on a porous support. Typical support materials include amorphous or crystalline oxide materials such as alumina, silica, and silica-alumina. The metal content of the catalyst is often as high as about 20 weight percent for non-noble metals. Noble metals are usually present in amounts no greater than about 1 wt %.

A preferred hydrofinishing catalyst is a The M41S family of catalysts are mesoporous materials having high silica contents whose preparation is further described in J. Amer. Chem. Soc., 1992, 114, 10834. Examples included MCM-41, MCM-48 and MCM-50. Mesoporous refers to catalysts having pore sizes from 15 to 100 Angstroms. A preferred member of this class is MCM-41 whose preparation is described in U.S. Pat. No. 5,098,684. MCM-41 is an inorganic, porous, non-layered phase having a hexagonal arrangement of uniformly-sized pores. The physical structure of MCM-41 is like a bundle of straws wherein the opening of the straws (the cell diameter of the pores) ranges from 15 to 100 Angstroms. MCM-48 has a cubic symmetry and is described for example is U.S. Pat. No. 5,198,203 whereas MCM-50 has a lamellar structure. MCM-41 can be made with different size pore openings in the mesoporous range. The mesoporous materials may bear a metal hydrogenation component, which is at least one of Group 8, Group 9 or Group 10 metals. Preferred are noble metals, especially Group 10 noble metals, most preferably Pt, Pd or mixtures thereof.

The following examples will illustrate the improved effectiveness of the chilling tower operation according to the present invention, but are not meant to limit the present invention in any fashion.

Example

Tests were conducted using the Lasentec® probe on slurry samples of heavy lube grade feed stocks (270N, 330N, & 600N). The feed stocks were solvent dewaxed using the Dilchill$^{SM}$ process having four chilling towers. The performance of the four Dilchill$^{SM}$ towers crystallizers was examined through this technique. It was found that a plant filtration rate improvement of over 50% could be achieved on the 600N due to discoveries detailing the wax crystallization from using this method. These heavy grades are typically filtration limited in conventional lubes processing, but this methodology can also be applied to lighter grades, which are typically chilling limited by reducing the solvent used in dilution.

It was shown through plant simulated lab dewaxing, or leaf filtrations, that one of four Dilchill$^{SM}$ towers in a ketone dewaxing process was producing lower than average filtration rates and low oil yields. Note that oil yields are monitored through direct comparison of liquids to solids. Liquids to Solids (L/S) refers to the ratio of solvent plus oil divided by the dry wax in the wax cake, and calculated on a weight basis. It is an important quantity, since it can be shown from a material balance that a reduction in L/S leads to a higher DWO (dewaxed oil) yield in the plant, therefore lower values of L/S are advantageous. The four towers are labeled T-400, T-401, T-402, and T-403, with T-402 being the under-achieving tower. Table 1 shows the corresponding values for feed filtration rate (FFR) and L/S.

TABLE 1

| Dilchill Tower | Normalized FFR* | Normalized L/S* |
|---|---|---|
| T-400 | 0.731 | 1.147 |
| T-401 | 0.760 | 1.005 |
| T-402 | 0.496 | 1.365 |
| T-403 | 1.000 | 1.000 |

*Note that these value were measured in the lab and are normalized to the average value of the "best" performing tower, T-401.

Through further analysis it appeared that there was a blockage around the middle stage of the tower that was likely producing shock chilling in this region due to excessive cold solvent pooling in the area with the absence of proper mixing. The impact of shock chilling is that many wax crystals nucleate at the same instant with only a minimum amount of time for crystal growth to occur. These small crystals then filter much slower than crystals formed during a more moderate cooling environment giving them the possibility to grow. Initially the thought was that the low temperature at this stage was due to the loss of a solvent nozzle causing excess cold solvent flow to the area. Another hypothesis was that this blockage was a result of wax build-up in the region creating pooling of solvent and/or additional shearing of the wax crystals by the impellers, another potential cause of small, poor filtering crystals.

Figure 1:
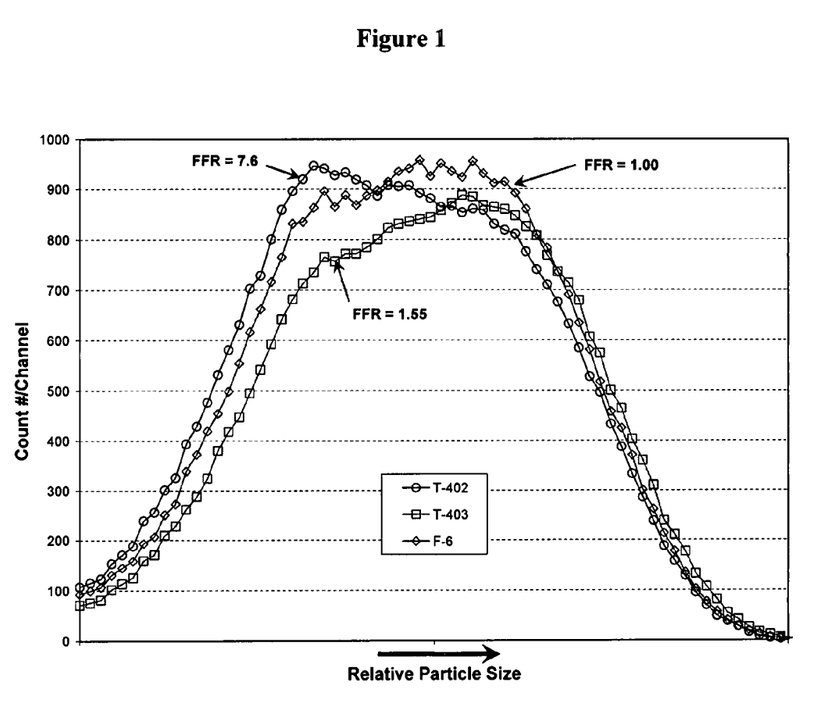
FIG. 1 is a graph showing the number of particle/crystal counts per channel versus the relative particle size for crystal size determination from towers T-402 and T-403.

In order to get a better grasp of the impact of the size of the wax crystals on the filtration performance, we employed the use of a Lasentec® FBRM Probe Model D600R particle size and population analyzer. This instrument measures the crystal size distribution (CSD) of the wax slurry, returning a breakdown of the number of particles (counts) per size range (channel). This gives a CSD showing the amount of particles present in the slurry that are ranging from small to large. A typical output is shown in FIG. 1, where the number of particle/crystal counts per channel is shown versus the relative particle size from small on the left side to large on the right. This figure shows that T-402 (circles) produced a higher amount of fine (small) crystals than it did coarse (large) crystals, designated by the slight "hump" on the left side of the trend. Compare this to the output from T-403 (squares) where the reverse is shown, there are more coarse than fine crystals. This supports the belief that the poorer tower is producing smaller crystals that reduce the filtration performance. This figure also shows the output from a sample taken directly after the feed collection drum F-6, where all of the wax slurry has been combined regardless of the Dilchill$^{SM}$ tower that it was produced in (diamonds). It can been seen that the general trend of the CSD has been greatly influenced by the presence of the increased number of fines produced in T-402, depicted by the flattening of the profile shown in the graph (diamonds) instead of an increase from left to right (squares).

Figure 2:
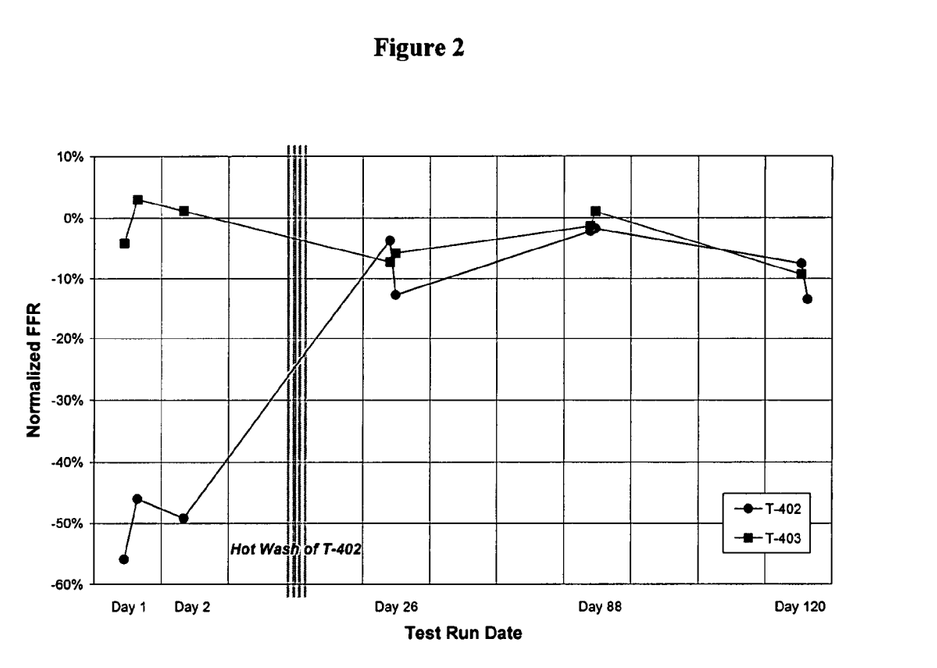
FIG. 2 is a graph showing the change in normalized feed filtration rate (FFR) over time for towers T-402 and T-403.
Figure 3:
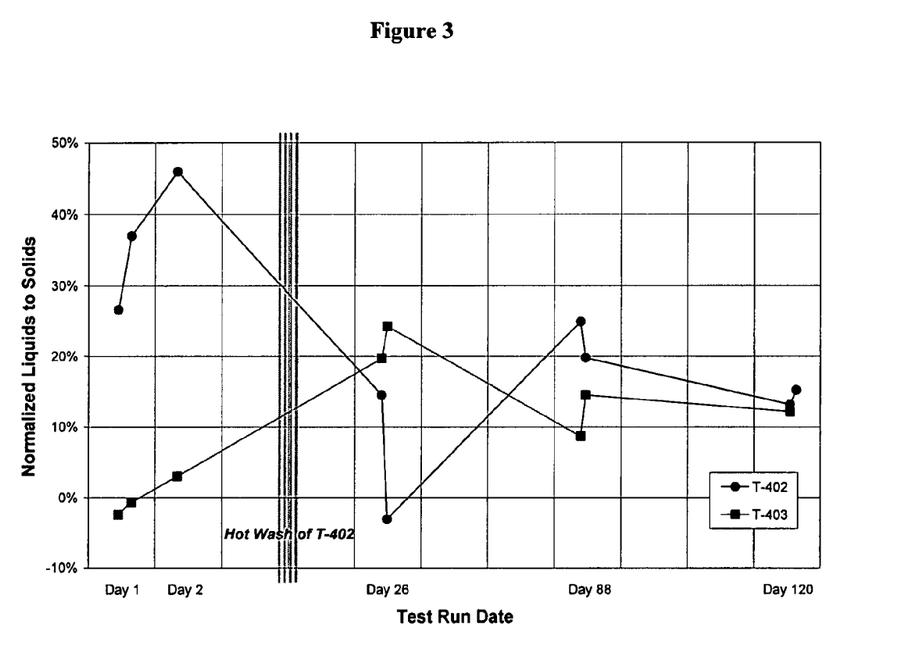
FIG. 3 is a graph showing the change in normalized liquids to solids ratio (L/S) over time for towers T-402 and T-403.

After this troubleshoot was completed, it was determined that T-402 needed a "hot wash" to clear out wax build-up in the tower that was impeding the crystallization process. Plant samples were taken from the bottoms of Dilchill$^{SM}$ towers T-402 & T-403 and returned to the lab for leaf filtrations over a period of four months. The data from these experiments provided values for FFR and L/S to compare the performance of the two towers over this time frame. This data has been normalized to the original values found on T-403 as a standard and is presented in FIGS. 2 & 3. FIG. 2 shows the change in normalized FFR over time for towers T-402 and T-403. FIG. 3 shows the change in normalized L/S over time for towers T-402 and T-403.

Figure 4:
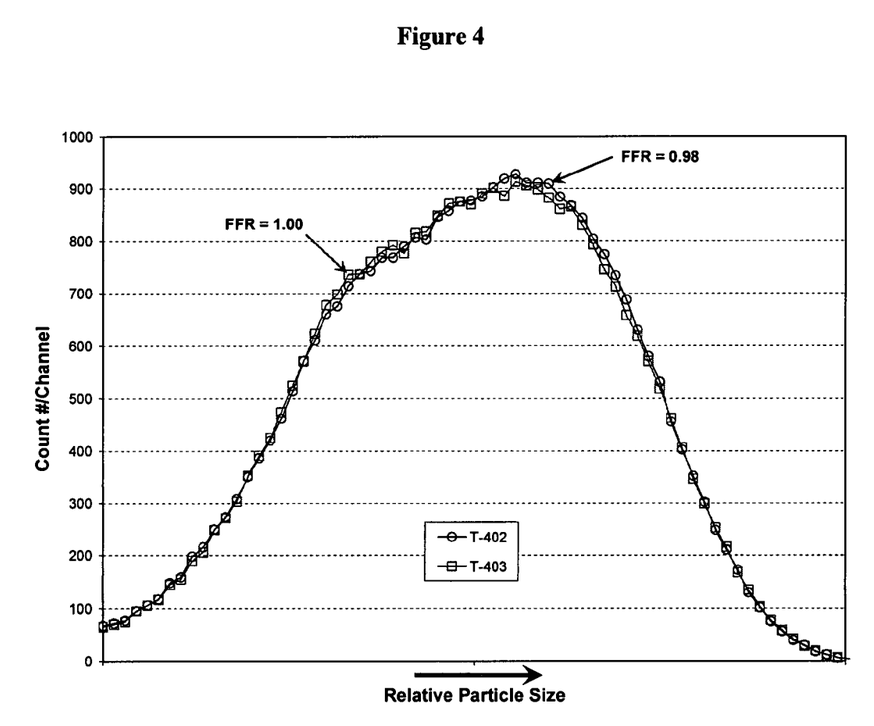
FIG. 4 is a graph showing the crystal size distribution for towers T-402 and T-403 after hot wash of tower T-402.

It is quickly evident that the hot washing of T-402 greatly improved its performance, to the point that it was likely producing wax crystals similar to those found in T-403 as shown in FIG. 4. When larger, stronger wax crystals are produced, then the filtration performance will go up due to the formation of better wax cakes. Of particular note is the increase in FFR of about 100%, jumping from a value of about 50% below the value of T-403 to almost an equal value. This improvement justified the belief that a wax build-up around the middle stage of the tower was the culprit in the poor performance observed.

Figure 5:
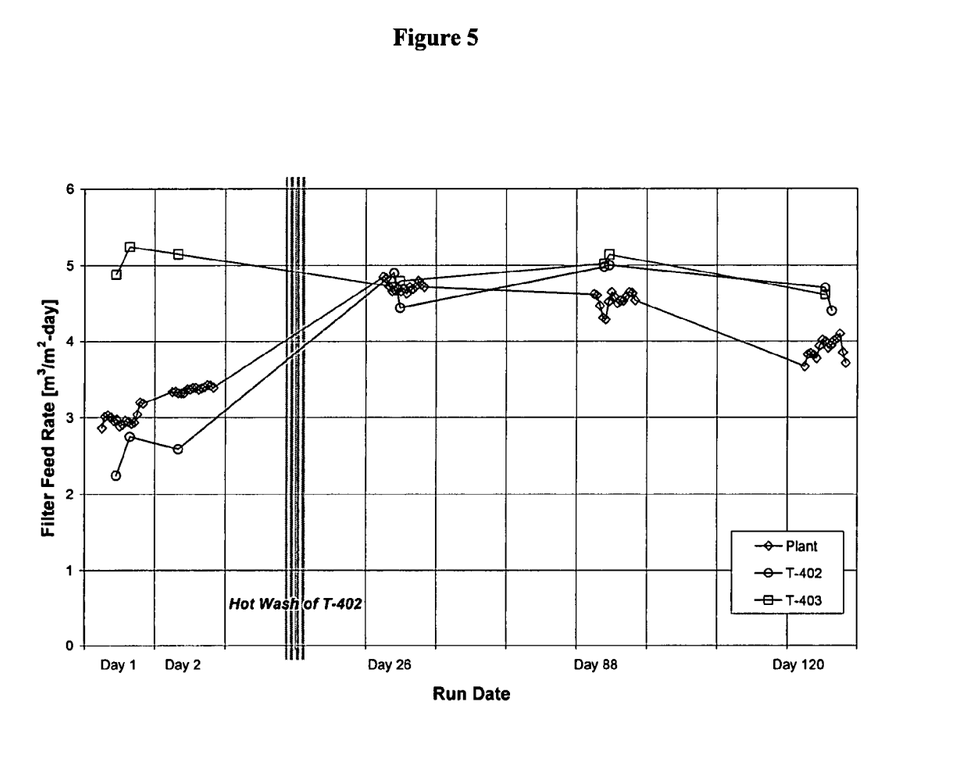
FIG. 5 is a graph showing a comparison over time of the FFR of towers T-402 and T-403 compared to the FFR calculated for the whole ketone dewaxing unit.

The impact of this improvement can be seen directly in the performance of the commercial ketone dewaxing unit as a whole. FIG. 5 shows a comparison over time of the FFR of the two towers in question along with the calculated value for the whole ketone dewaxing unit. It shows that early in the test, T-402 (circles) was performing poorly and consequently was drastically pulling down the performance of the whole unit (diamonds) regardless of the fact that the other three towers were performing well (T-403 shown as squares). This is consistent with previous experience that found a debit in FFR of about 60% of the total FFR attributed to the poorer performing tower, while the other towers only make up the remaining 40% of the total MEK unit's performance. The theory behind this phenomenon is that the poor performing tower was creating smaller wax crystals that when mixed with the output of the other towers would then contaminate the feed to all of the filters. These small crystals would effectively clog the filter cloth, reducing the ability of the filtrate to penetrate the filter medium, causing a reduction in the FFR value and also causing more oil and solvent to remain in the wax, raising the L/S value. With the cleaning of T-402 and the improvement in its performance, there is no longer as many small crystals contaminating the unit and the performance jumps to about a 50% increase of its output from before the hot wash, as seen in FIG. 5 during the Day 26 testing.

In order to grasp the benefits of using this invention to monitor and identify when to hot wash the Dilchill$^{SM}$ towers, a look at the capacity improvement can be conducted. Since these tests were only conducted during 600N runs and heavy grades are typically filtration limited while the light grades are typically chilling limited, the benefits of hot washing a "poor" tower was only considered for the heavier grade runs. If we consider a modest improvement of 15% additional throughput for the unit, this means an additional 5.1 kbd capacity for the ketone dewaxing unit. This is based on the approximate capacities for heavy grades shown in Table 2. This number jumps to 17 kbd if you consider the improvement made between Day 2 and Day 26 of about a 50% jump in performance due to the hot washing of T-402. These numbers are based on a relative basis and should not be considered as a definite capacity increase but as potentially achievable capacity increases. It should be noted that even though the light grades are chilling limited, that monitoring the tower performance and subsequent hot washing of towers with wax build-up could cause an improvement in the DWO yield (L/S) for the light grades. This allows for a potential benefit to exist with these grades as well, although this would need to be demonstrated in order to determine any possible capacity increases before any estimates can be generated.

TABLE 2

| Grade Run | Typical Capacity | 15% Improvement | 50% Improvement |
|---|---|---|---|
| 600N | 13.0 kbd | 1.95 kbd | 6.50 kbd |
| 330N | 16.5 kbd | 2.48 kbd | 8.25 kbd |
| 270N | 4.5 kbd | 0.68 kbd | 2.25 kbd |
| Total | 34.0 kbd | 5.11 kbd | 17.0 kbd |

The invention claimed is:

1. A process for on-line monitoring of wax crystal formation in solvent dewaxing equipment for use in lubricant oil production, said solvent dewaxing equipment including at least one chilling tower, which comprises: conducting a waxy feedstock to the at least one chilling tower having at least one inlet and outlet, contacting the waxy feedstock with chilled dewaxing solvent to form a mixture of solvent, oil and wax crystals, conducting the mixture from the at least one chilling tower outlet to a separator provided that wax crystal size distribution of the wax crystals in the mixture is measured prior to entering the separator using an on-line particle size analyzer, and separating wax crystals from oil and solvent.

2. A solvent dewaxing process for the preparation of lubricant oils from a waxy feedstock which comprises: conducting the waxy feedstock to at least one chilling tower having at least one inlet and outlet, contacting the waxy feedstock with dewaxing solvent in at least one chilling zone in the chilling tower under mixing conditions to form a mixture of wax crystals, solvent and oil, conducting the mixture from the at least one chilling tower outlet to a separator provided that wax crystal size distribution of the wax crystals in the mixture is measured prior to entering the separator using an on-line particle size analyzer, separating wax crystals from oil and solvent, and adjusting conditions as needed in the at least one chilling tower to modify wax crystal size to improve separation of wax crystals.

3. The process of claim 1 or 2 wherein the waxy feedstock has been solvent extracted.

4. The process of claim 1 or 2 wherein the waxy feedstock has been hydrotreated.

5. The process of claim 1 or 2 wherein the waxy feedstock is contacted with chilled dewaxing solvent using dilution chilling dewaxing.

6. The process of claim 1 or 2 wherein the dewaxing solvent comprises at least one of aliphatic ketones having 3-6 carbon atoms, low molecular weight $C_3$-$C_6$ hydrocarbons, and aromatic solvents.

7. The process of claim 6 wherein the aliphatic ketone is at least one of methyl ethyl ketone and methyl isobutyl ketone, the low molecular weight $C_3$-$C_6$ hydrocarbon is at least one of propane and butane, and the aromatic solvent is at least one of benzene, toluene, or xylene.

8. The process of claim 1 or 2 wherein the separator is at least one of rotary drum filter, membrane filter, filter cloth or centrifuge.

9. The process of claim 1 or 2 wherein the on-line particle size analyzer is located between the at least one chilling tower outlet and the separator.

10. The process of claim 9 wherein the on-line particle analyzer is located at or near the at least one chilling tower outlet.

11. The process of claim 2 wherein adjusting conditions in the chilling tower includes at least one of hot washing the chilling tower, increasing impeller speed, adjusting solvent flow and temperature and changing temperature profile down the chilling tower.

12. The process of claim 11 wherein adjusting solvent flow is by increasing solvent flow.

13. The process of claim 8 wherein the separator is a rotary drum filter or a membrane filter.

14. The process of claim 2 wherein filtration rate from the separator and yield of base oil are correlated with the wax crystal size distribution.

15. The process of claim 14 wherein overall profitability of the dewaxing process is improved by adjusting the wax crystal size distribution to maximize throughput, maximize yield and/or reduce energy.

16. The process of claim 14 wherein the throughput is either filtration limited or chilling limited.

17. The process of claim 14 wherein filtration rate is adjusted by adjusting the wax crystal size distribution in the at least one chilling tower.

18. The process of claim 17 wherein the wax crystal size distribution has properties including a) narrow distribution of wax crystal sizes, b) large mean crystal size, c) spherical crystal shape, and d) hard wax crystals.

19. The process of claim 17 wherein the wax crystal size distribution in the at least one chilling tower is adjusted by adjusting at least one of 1) predilution ratio, 2) slop to feed ratio, 3) tower inlet temperature, 4) agitator speed, 5) tower dilution ratio, 6) tower temperature profile, 7) solvent composition, 8) solvent flow profile, 9) solvent temperature(s), 10) dewaxing aid ratio, and 11) dewaxing aid rate.

20. The process of claim 2 wherein the oil and solvent from the separator are further separated to produce an oil.

21. The process of claim 20 wherein the oil is hydrofinished.

* * * * *